United States Patent [19]  [11] 4,368,148
Bohn  [45] Jan. 11, 1983

[54] PROTEIN PP9, PROCESS FOR ITS ENRICHMENT AND ITS ISOLATION AND ITS USE

[75] Inventor: Hans Bohn, Marburg, Fed. Rep. of Germany

[73] Assignee: Behringwerke Aktiengesellschaft, Marburg, Fed. Rep. of Germany

[21] Appl. No.: 252,089

[22] Filed: Apr. 8, 1981

[30] Foreign Application Priority Data

Jan. 10, 1980 [DE] Fed. Rep. of Germany ....... 3013724

[51] Int. Cl.³ .................. A61K 35/50; A61K 39/395; C07G 7/00
[52] U.S. Cl. ............................ 260/112 B; 260/112 R; 424/85; 424/105
[58] Field of Search ...................... 260/112 B, 112 R; 424/105, 85

[56] References Cited

U.S. PATENT DOCUMENTS

| 3,931,399 | 1/1976 | Bohn et al. | 424/105 |
| 4,018,885 | 4/1977 | Bohn et al. | 260/112 R |
| 4,041,021 | 8/1977 | Bohn | 260/112 B |
| 4,065,445 | 12/1977 | Bohn et al. | 260/112 B |
| 4,191,533 | 3/1980 | Bohn et al. | 260/112 B X |
| 4,254,021 | 3/1981 | Bohn et al. | 260/112 B |
| 4,297,274 | 10/1981 | Bohn et al. | 260/112 B |
| 4,297,343 | 10/1981 | Bohn et al. | 260/112 B X |

FOREIGN PATENT DOCUMENTS 1555197 11/1979 United Kingdom .

Primary Examiner—Howard E. Schain
Attorney, Agent, or Firm—Curtis, Morris & Safford

[57] ABSTRACT

What are disclosed are a protein, PP9, useful for the diagnosis and monitoring of diseases involving tissue degradation, and a method for its isolation, said protein having:

(a) a content of carbohydrates of 5.57±1.35%, of which are 4.9±1.0% hexoses, 0.1±0.1% hexoseamines, 0.07±0.05% fucose and 0.5±0.20% neuraminic acid;
(b) a sedimentation coefficient $S_{20,W}$ of 3.2±0.2 S;
(c) a molecular weight of 35,100±3,800 determined in the ultracentrifuge;
(d) a molecular weight of 40,000±4,000 determined in sodium dodecylsulfate (SDS)-containing polyacrylamide gel;
(e) an extinction coefficient $E_1^{1\%}$ $_{cm}$ (280 nm) of 14.6±1.0;
(f) an electrophoretic mobility in the range of the $\beta_1$-globulins; and
(g) an isoelectric point in a pH range of 5.0-6.8.

3 Claims, 2 Drawing Figures

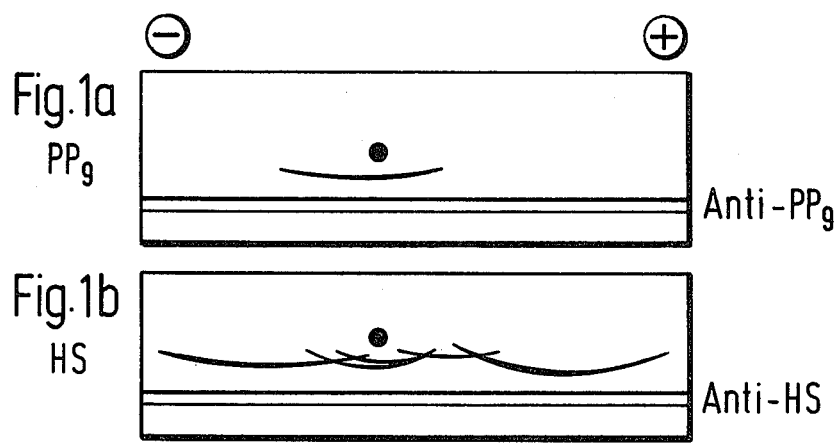

PROTEIN PP9, PROCESS FOR ITS ENRICHMENT AND ITS ISOLATION AND ITS USE

The invention relates to a new protein (PP9), to a process for its enrichment and its isolation and its use.

PP9 is present in almost all of the human organs investigated up to now, especially in the placenta of humans. It was detected in the following fetal organs: heart, liver, kidneys, lungs, stomach, brain, and further more in the following adult organs: heart, lungs, stomach, kidneys, uterus, liver, spleen, adrenal gland, colon and bladder.

In general, about 42 mg of this protein can be extracted with a physiological salt solution from a human term placenta (600 g). The concentration of PP9 in other human organs is assumed to be of similar magnitude. In the serum, PP9 is normally not present or is present in traces only (<0.1 mg per 100 ml).

The ubiquitous tissue protein PP9 is characterized by
(a) a content of carbohydrates of 5.57±1.35%, of which are 4.9±1.0% hexoses, 0.1±0.1% hexoseamines, 0.07±0.05% fucose and 0.5±0.20% neuraminic acid;
(b) a sedimentation coefficient $S_{20,w}$ of 3.2±0.2 S;
(c) a molecular weight of 35,100±3,800 determined in the ultracentrifuge;
(d) a molecular weight of 40,000±4,000 determined in sodium dodecylsulfate (SDS)-containing polyacrylamide gel;
(e) an extinction coefficient $E_1\ _{cm}^{1\%}$ (280 nm) of 14.6±1.0;
(f) an electrophoretic mobility in the range of the $\beta_1$-globulins; and
(g) an isoelectric point in the pH range of 5.0–6.8.

The following explanations serve to illustrate the characteristics of the tissue protein.

Determination of the sedimentation coefficient was carried out in an analytic ultra-centrifuge of Messrs. Beckmann (Spinco-apparatus, model E) at 60,000 rev./min. in double sector cells with the aid of UV-scanner technique at 280 nm. As the solvent, a 0.05 M phosphate buffer (pH 6.8), containing 0.2 mole/l NaCl, was used. The protein concentration was adjusted to an optical density (O.D.) of about 3. The sedimentation coefficients were calculated on the basis of water at 20° C.

For determining the molecular weight in the ultracentrifuge, the sedimentation equilibrium method was used. The concentration of the protein was adjusted for this purpose to about 1.0 O.D. The determination was effected at 9,000 rev./min. Registration was effected with ultraviolet optics at 280 nm using a photoelectric scanner.

For determining the molecular weight in SDS-PAA gel, a gel containing 7.5% of polyacrylamide (PAA) and 0.1% of sodium dodecyl sulfate (SDS) was used. As the comparative substance, human placenta-lactogen (HPL) and human albumin as well as their aggregates were used.

For determining the extinction coefficients, the substance was dissolved to a strength of 0.10% (w/v) in distilled water.

The test for the electrophoretic mobility was carried out on cellulose acetate foils of Messrs. Sartorius with a sodium diethyl barbiturate buffer of pH 8.6, using the micromodification, by means of the apparatus Microzone R 200 of Messrs. Beckmann Instruments.

Determination of the isoelectric point was made on a column (440 ml) of Messrs. LKB, Stockholm. The so-called ampholine mixture had a pH-range from 5.0 to 7.0. The protein PP9 is very heterogeneous. In isoelectric focussing, it appears in a pH range of 5.0–6.8, the main quantity of the protein appearing in a pH range of 6.4–6.7.

Determination of the carbohydrates was carried out according to the method described by H. E. Schultze, R. Schmidtberger, and H. Haupt, Biochem. Z. 329, page 490 (1958).

The analysis for amido-acids was carried out according to the method described by S. Moore, D. H. Spackman, and W. H. Stein, Anal. Chem. 30, 1185 (1958), using the liquid chromatograph Multichrom B of Messrs. Beckmann.

½-Cystine was determined, after oxidation of the protein, with per-formic acid [S. Moore et al., Anal.Chem. 30, 1185 (1958)] and subsequent chromatography [S. Moore, J.Biol. Chem., 238, 235 (1963)] as cysteinic acid. The content of tryptophan was determined by the direct photometric test method, according to H. Edelhoch, Biochemistry 6, 1948 (1967).

The results of the analysis for amino-acids of PP9 obtained according to the Example are listed in Table I.

TABLE I

Amino-acid composition of PP9

| | (residues per 100 residues) (Mol %) | Variation coefficient (VC) (%) |
|---|---|---|
| Lysine | 8.04 | 3.49 |
| Histidine | 2.58 | 5.06 |
| Arginine | 3.49 | 1.8 |
| Aspartic acid | 10.30 | 10.45 |
| Threonine | 4.29 | 9.82 |
| Serine | 5.7 | 10.77 |
| Glutamic acid | 11.18 | 2.15 |
| Proline | 6.17 | 13.61 |
| Glycine | 5.50 | 0.79 |
| Alanine | 5.69 | 1.11 |
| Cystine/2 | 2.29 | 4.38 |
| Valine | 7.12 | 2.58 |
| Methionine | 1.47 | 9.64 |
| Isoleucine | 5.28 | 5.28 |
| Leucine | 10.55 | 3.23 |
| Tyrosine | 3.95 | 9.68 |
| Phenylalanine | 3.87 | 5.48 |
| Tryptophan | 2.36 | 0.69 |

The following properties of PP9 were found which may be useful for isolating this novel tissue protein:

(1) with ammonium sulfate, PP9 is precipitated at pH 7.0, in a saturation of between 30% and 60%, from aqueous solutions:

(2) PP9 is precipitated with water-soluble acridine bases, for example 2-ethoxy-6,9-diaminoacridine lactate (Rivanol ®) at pH-values between 7 and 9 and a concentration of 0.4 to 0.8% w/v. However, it is not precipitated or it is precipitated to a small extent only at a pH of 6.0, if the Rivanol concentration is ≦0.4%.

(3) In precipitations with ethanol, the main quantity of PP9 in physiological salt solutions at pH 7.0 up to a concentration of 25% of alcohol is to be found in the supernatant.

(4) In preparative electrophoresis, PP9 migrates in the range of the $\beta_1$-globulins.

(5) In gel-filtration using Sephadex ®, PP9 appears in the range of proteins having molecular weights of between 20,000 to 60,000.

(6) PP$_9$ is adsorbed on weakly basic ion exchangers, for example DEAE-cellulose or DEAE-Sephadex, using buffers of low conductivity (about 0-2 mS) and neutral or weakly alkaline pH-values (about pH 7 to 9).

(7) PP$_9$ can be enriched and isolated from its aqueous solution by immuno-adsorption.

The invention furthermore relates to a process for isolating PP$_9$ which comprises fractionating a solution, which contains this protein, on the basis of the above-described properties.

In addition to ammonium sulfate, other neutral salts commonly used in preparative biochemistry can be used for precipitating PP$_9$. Besides acridine bases, water-soluble derivatives of a quinoline base, used in protein fractionation, may be used within the process of the present invention. Corresponding to its electrophoretic behaviour and the molecular weight, also other measures which are suitable for separating a $\beta_1$-globulin or a protein having a molecular weight of about 40,000 from other proteins can be used for isolating the protein. The various methods of gel-filtration, gel-chromatography or ultra-filtration may be used for this purpose. This is evident in view of the property of PP$_9$ of attaching itself onto weakly basic ion exchangers and of being eluted therefrom again.

The PP$_9$ can be isolated by using a selected combination of the above-described measures, which, on the one hand, enrich PP$_9$ and, on the other hand, permit separation of this protein from the other proteins.

Accordingly, a further feature of the invention are the individual steps for enriching PP$_9$ and the methods for purifying PP$_9$ resulting from a combination of the measures for enrichment.

The process for the enrichment is characterized by that at least one of the measures (1) to (7) mentioned earlier herein or their chemical or biochemical preparative equivalents are used.

Still another feature of the invention is a process for preparing PP$_9$ which comprises subjecting a liquid, which contains this protein to one or several known steps for the isolation of proteins and isolating in each case the material, wherein the protein having the characteristic properties of PP$_9$ is enriched.

For detecting and for determining the PP$_9$, for example in a fraction from a separation step, immuno-chemical methods may be used, in addition to the above-described parameters, since PP$_9$ has antigenic properties.

An antiserum suitable for this purpose may be prepared in the following manner: A polyvalent antiserum, with the aid of which PP$_9$ can be detected, is obtainable by immunization of rabbits with a PP9-containing placenta protein fraction [placenta fractions III and V according to Bohn H., Arch.Gynäk. 210, 440 (1971)]. This antiserum may be rendered substantially specific against the antigen PP$_9$ by absorption with normal human serum and those placenta fractions that do not contain PP$_9$. The resulting specific antiserum can be used on the one hand for the immunologic detection of PP$_9$ and on the other hand for the preparation of an immuno-absorbent, which latter can be used in the enrichment and isolation of PP$_9$.

The immunologic detection of PP$_9$ may be carried out with the aid of the gel diffusion technique according to Ouchterlony (cf. Schultze and Heremans, Molecular Biology of Human Proteins, vol. 1, page 134).

Monospecific antisera may be prepared by immunization of animals according to known methods using the PP$_9$ obtained according to the present invention.

PP$_9$ has antigenic properties. If animals are immunized with this protein, specific antibodies are formed. FIG. 1a shows the immunologic reaction of PP$_9$ with a specific anti-serum of rabbits, after separation in an electric field in agar-containing gel. For comparative reasons, FIG. 1b shows the separation of the serum proteins, which separation has been rendered visible by the immuno-reaction of the proteins with an antiserum of rabbits against human serum (HS).

The detection and the determination of PP$_9$ by immunological methods is important in diagnostics. Obviously, PP$_9$ is a tissue protein which is present in almost all human organs. In the case of diseases which involve tissue disintegration, this protein, present in the blood, then has a higher concentration. Therefore, the determination of the protein PP$_9$ can be used generally for the detection of diseases for following up the course of the disease as well as for the control of the therapy.

PP$_9$ can therefore be used for the preparation of antisera, which are suitable for detecting and determining PP$_9$.

The invention is illustrated by the following Example:

EXAMPLE (A) Extraction of placentas and fractionation of the extract with Rivanol and ammonium sulfate 1000 kg of deep-frozen human placentas are comminuted in a cutter-mixer and extracted with 1000 l of a 0.4% w/v strength NaCl-solution. After separation of the tissue residue by centrifugation, the extract is adjusted to pH 6.0 by means of 20% acetic acid and combined, while stirring, with 200 l of a 3% strength solution of 2-ethoxy-6,9-diaminoacridine-lactate (Rivanol ®, Hoechst AG). The precipitate formed is centrifuged off and rejected. To the supernatant there is added 1 w/v % of Bentonit A of Messrs. Erbslöh & Co. of Geisenheim/Rhein, the pH of the resulting product is adjusted to 7.0 by adding 2 N NaOH and the product is filtered. To the filtrate there is slowly added, while stirring, 30 w/v % of ammonium sulfate, the placental protein PP$_9$ precipitating during this operation together with other proteins. Filtration of the precipitate gives about 12 kg of a damp paste, which is hereinafter named fraction A. 500 g of this paste contain on the average about 640 mg of PP$_9$.

(B) Gel filtration on Sephadex G-150

500 g of the fraction A are dissolved in about 400 ml of water and dialyzed against a 0.1 M Tris-HCl buffer of pH 8.0 containing 1.0 mol/l of NaCl and 0.1% of NaN$_3$ (buffer solution I).

The protein-containing solution is applied to a column (20×100 cm) charged with Sephadex G-150 and is subjected to a gel filtration. Buffer solution I is used for the elution. The eluates are tested by the gel diffusion test according to Ouchterlony with the aid of a specific anti-PP$_9$-rabbit serum. All fractions containing the placental protein PP$_9$ are collected and subsequently concentrated on an ultrafilter (Amicon UF 2000) to about 300 ml using PM 10 membranes. The resulting solution (fraction B) contains altogether about 600 mg of PP$_9$.

(C) Enrichment of PP9 by immuno-adsorption

1. Preparation of the immuno-adsorbent 350 ml of anti-PP9 serum from rabbit are dialyzed against a 0.02 M phosphate buffer (pH 7.0) and chromatographed on DEAE-cellulose to separate the immunoglobulins. The immunoglobulin fraction (2.78 g of protein) is then reacted with 278 g of especially purified agarose in spherical form (Sepharose ® 4 B of Pharmacia, Uppsala, Sweden) which had been activated with 348 g of cyanogen bromide and is thus bound covalently onto a carrier.

This process is described by Axen, R., Porath, J., and Ernbach, S., Nature, 214, 1302 (1967).

The placenta protein PP9 can be isolated from its solutions, especially from its PP9-enriched placenta extract fractions, by means of the immuno-adsorbent prepared in this manner.

2. Carrying out the immuno-adsorption

The immuno-adsorbent is suspended in a 0.1 M Tris-HCl buffer (pH 8.0) containing 1.0 mol/l of NaCl and 0.1% of $NaN_3$ (hereinafter referred to as buffer solution I), then filled into a column for chromatography (5.5×20 cm) and rinsed with the buffer I. Then, 60 ml of the PP9-containing solution (fraction B) are slowly passed through the column, whereby PP9 is bound immuno-adsorptively. The column is thoroughly washed with buffer I and the adsorbed protein is eluted with about 600 ml of a 3 M potassium thiocyanate solution. The PP9-containing eluates are dialyzed against the buffer solution I and concentrated to about 15 ml in an ultrafilter. Yield per adsorption: ~10 mg of PP9.

Directly after the elution of PP9, the adsorbent in the column is neutralized with the buffer solution I and washed thoroughly; it can then be used again for the immuno-adsorptive fixation of PP9.

(D) High purification of PP9

The protein obtained by immuno-adsorption is often contaminated by unspecifically bound serum proteins and by other tissue proteins from placenta. Separation of the main quantity of these accompanying serum proteins is made, for example, by gel-filtration on Sephadex G-150. The remaining serum proteins can be removed by inverse or negative immuno-adsorption, i.e. with the aid of carrier-bound antibodies against the serum proteins present as contamination.

For example, the proteins $SP_1$ [cf. Bohn, H. et al. Blut 32, 103 (1976)] and $PP_7$ [Bohn, H. and Winckler, W., Blut 25, 305 (1977)], present in small amounts were removed by corresponding immuno-absorbents. In addition to these known proteins, some other placental tissue proteins heretofore unknown were also detected in the PP9 crude fraction. To prepare antibodies against these accompanying proteins, the PP9 crude fraction was dialyzed for 12 hours against a 0.5 M glycine-HCl buffer of pH 2.5, followed by neutralization. Under these conditions PP9 is denatured and loses its immunochemical reactivity. The contaminants, however, are stable and may be maintained as antigens. If animals are immunized with these antigens, there are formed antibodies against these proteins, which, after fixation on a carrier, may be used for the immuno-absorptive removal of unknown placental proteins from the PP9 crude fraction.

What is claimed is:

1. An isolated, concentrated tissue protein, PP9, obtained by fractionating an extract of human organs or a solution obtained from such an extract, said tissue protein having:
   (a) a content of carbohydrates of 5.57±1.35% consisting of 4.9±1.0% of hexoses, 0.1±0.1% of hexosamines, 0.07±0.05% of fucose, and 0.5±0.20 of neuraminic acid;
   (b) a sedimentation coefficient $S_{20,W}$ of 3.2±0.2 S;
   (c) a molecular weight of 35,100±3,800 determined in an ultracentrifuge;
   (d) a molecular weight of 40,000±4,000 determined in a polyacrylamide gel containing sodium dodecyl sulfate;
   (e) an extinction coefficient $E_1\ _{cm}^{1\%}$ (280 nm) of 14.6±1.0;
   (f) an electrophoretic mobility in the range of the $\beta_1$-globulins;
   (g) an isoelectric point in a pH range of 5.0–6.8; and
   (h) an amino acid analysis of

|  | Mol % | Variation coefficient (%) |
|---|---|---|
| Lysine | 8.04 | 3.49 |
| Histidine | 2.58 | 5.06 |
| Arginine | 3.49 | 1.8 |
| Aspartic acid | 10.30 | 10.45 |
| Threonine | 4.29 | 9.82 |
| Serine | 5.7 | 10.77 |
| Glutamic acid | 11.18 | 2.15 |
| Proline | 6.17 | 13.61 |
| Glycine | 5.50 | 0.79 |
| Alanine | 5.69 | 1.11 |
| Cystine/2 | 2.29 | 4.38 |
| Valine | 7.12 | 2.58 |
| Methionine | 1.47 | 9.64 |
| Isoleucine | 5.28 | 5.28 |
| Leucine | 10.55 | 3.23 |
| Tyrosine | 3.95 | 9.68 |
| Phenylalanine | 3.87 | 5.48 |
| Tryptophan | 2.36 | 0.69 |

2. A tissue protein as in claim 1 obtained by fractionating an extract of human placentas.

3. An antiserum to the tissue protein of claim 1 obtained by injecting said tissue protein into an animal, taking the blood of the animal after some time, and recovering the serum from said blood.

* * * * *

UNITED STATES PATENT OFFICE
CERTIFICATE OF CORRECTION

Patent No. 4,368,148　　　　　　Dated January 11, 1983

Inventor(s) Hans Bohn

It is certified that error appears in the above-identified patent and that said Letters Patent are hereby corrected as shown below:

On the title page:

Item [30], the date "Jan. 10, 1980" should be -- April 10, 1980 --.

Signed and Sealed this

Fifth Day of April 1983

[SEAL]

Attest:

Attesting Officer

GERALD J. MOSSINGHOFF

Commissioner of Patents and Trademarks